United States Patent
Shen et al.

(10) Patent No.: US 9,247,862 B2
(45) Date of Patent: Feb. 2, 2016

(54) METHOD FOR MANUFACTURING VISIBLE PUNCTURE OUTFIT FOR DISPOSABLE LAPAROSCOPE AND PUNCTURE OUTFIT USING THE METHOD

(75) Inventors: Zhenquan Shen, Guangdong (CN); Chengjun Gou, Guangdong (CN); Zhitan Yan, Guangdong (CN); Zhenning Huang, Guangdong (CN)

(73) Assignee: DONGGUAN MICROVIEW MEDICAL TECHNOLOGY CO., LTD, Guangdong (CN)

( * ) Notice: Subject to any disclaimer, the term of this patent is extended or adjusted under 35 U.S.C. 154(b) by 133 days.

(21) Appl. No.: 14/002,739

(22) PCT Filed: Aug. 14, 2012

(86) PCT No.: PCT/CN2012/080092
§ 371 (c)(1),
(2), (4) Date: Sep. 3, 2013

(87) PCT Pub. No.: WO2013/063968
PCT Pub. Date: May 10, 2013

(65) Prior Publication Data
US 2013/0338435 A1 Dec. 19, 2013

(30) Foreign Application Priority Data
Nov. 1, 2011 (CN) .......................... 2011 1 0338794

(51) Int. Cl.
*A61B 1/00* (2006.01)
*A61B 17/34* (2006.01)
(Continued)

(52) U.S. Cl.
CPC ........... *A61B 1/00087* (2013.01); *A61B 1/0011* (2013.01); *A61B 17/3417* (2013.01);
(Continued)

(58) Field of Classification Search
USPC ......... 600/106–107, 114–115, 146, 210, 217; 604/164.01–164.04
See application file for complete search history.

(56) References Cited

U.S. PATENT DOCUMENTS 4,254,762 A * 3/1981 Yoon .............................. 600/114
5,147,316 A * 9/1992 Castillenti ................ 604/164.04
(Continued)

FOREIGN PATENT DOCUMENTS

WO WO 2007035937 A1 3/2007
WO WO 2009012547 A2 1/2009

*Primary Examiner* — Matthew J Kasztejna

(57) ABSTRACT

This invention discloses a method for manufacturing a disposable endoscopic puncture outfit for laparoscopy operations. The manufacturing method comprises the following steps: 1) preparing a camera shooting module; 2) preparing a puncture needle; 3) preparing a positioning puncture casing pipe; 4) mounting the camera shooting module on the puncture needle; 5) inserting the puncture needle in the positioning puncture casing pipe, and making a transparent cover slightly extend out of the positioning puncture casing pipe. This invention also discloses a puncture outfit made with a method for manufacturing a disposable endoscopic puncture outfit for laparoscopy operations. The manufacturing method provided by this invention has a simple process, is easy to implement, and has high production efficiency. The puncture outfit provided by this invention has a reasonable structure, can be used for visible surgical procedures through the camera shooting module, and can effectively improve the safety of the puncture surgery and reduce the medical negligence. Moreover, the operation becomes simple in a visible state, relies less on the skill of a surgeon, and the accuracy and success rate of the surgery can be increased.

3 Claims, 6 Drawing Sheets

(51) Int. Cl.
*A61B 19/00* (2006.01)
*A61B 17/00* (2006.01)

(52) U.S. Cl.
CPC ......... *A61B17/3496* (2013.01); *A61B 19/5212* (2013.01); *A61B 2017/00907* (2013.01); *A61B 2017/3454* (2013.01); *Y10T 29/49826* (2015.01)

(56) References Cited

U.S. PATENT DOCUMENTS

| | | | |
|---|---|---|---|
| 5,256,149 A * | 10/1993 | Banik et al. | 604/164.01 |
| 5,330,497 A * | 7/1994 | Freitas et al. | 606/185 |
| 5,334,150 A * | 8/1994 | Kaali | 604/164.08 |
| 5,467,762 A * | 11/1995 | Sauer et al. | 600/114 |
| 5,569,292 A * | 10/1996 | Scwemberger et al. | 606/185 |
| 5,674,184 A * | 10/1997 | Hassler, Jr. | 600/176 |
| 5,817,061 A * | 10/1998 | Goodwin et al. | 604/164.03 |
| 5,857,999 A * | 1/1999 | Quick et al. | 604/107 |
| 6,001,084 A * | 12/1999 | Riek et al. | 604/272 |
| 6,387,043 B1 * | 5/2002 | Yoon | 600/109 |
| 6,451,042 B1 * | 9/2002 | Bonutti | 606/190 |
| 6,527,704 B1 * | 3/2003 | Chang et al. | 600/112 |
| 7,927,272 B2 * | 4/2011 | Bayer et al. | 600/129 |
| 8,608,769 B2 * | 12/2013 | Kahle et al. | 606/190 |
| 2008/0243162 A1 * | 10/2008 | Shibata et al. | 606/185 |
| 2009/0043167 A1 * | 2/2009 | Leiner | 600/156 |
| 2010/0081875 A1 | 4/2010 | Fowler et al. | |
| 2010/0324369 A1 * | 12/2010 | Smith | 600/138 |

* cited by examiner

METHOD FOR MANUFACTURING VISIBLE PUNCTURE OUTFIT FOR DISPOSABLE LAPAROSCOPE AND PUNCTURE OUTFIT USING THE METHOD

A method for manufacturing disposable endoscopic puncture outfit for laparoscopy operations and a puncture outfit using the method.

This invention pertains to the technical field of medical apparatus and particularly to a method for manufacturing a disposable endoscopic puncture outfit for laparoscopy operations and a puncture outfit using the method.

The minimally invasive surgery represented by laparoscope has developed rapidly in recent years. The surgery quantity has been more than that of traditional surgery in developed countries. The minimally invasive treatment technologies characterized by minor surgery and minor wound have gradually been recognized by extensive surgeons. Casing pipe puncture outfit is a necessary apparatus to set up surgical and observation channels in laparoscopic surgery. However, the existing casing pipe has no visible function. That is, "blind placement" is adopted. The surgeons carry out the surgery all by their experience. During the puncture process, the artery blood vessels such as retroperitoneal aorta and artery blood vessels of abdominal wall cannot be seen or touched in blind placement. Therefore, it is operated inconveniently. In case of injuries, it usually results in fatal hemorrhoea and surgery incidents. Moreover, the normal tissues of visceral organs are easily injured accidentally such as vascular, intestine and bladder injuries when the casing pipe puncture outfit is inserted in the abdominal cavity. There is a hidden danger for laparoscopic surgery complications, which can hardly guarantee the surgery safety and effectiveness.

BRIEF SUMMARY OF THE INVENTION

In allusion to the above shortcomings, one of the purposes for this invention is to provide a method for manufacturing a disposable endoscopic puncture outfit for laparoscopy operations that features simple process, easy implementation, high efficiency and effectiveness.

The other purpose for this invention is to provide a puncture outfit that features is designed with reasonable structure, can be visible throughout the surgery and is operated conveniently.

To realize the above purposes, the technical solutions provided by this invention include:

A method for manufacturing a disposable endoscopic puncture outfit for laparoscopy operations, characterized in that it comprises the following steps:

(1) Prepare a camera shooting module with light source;
(2) Prepare a puncture needle;
(3) Prepare a positioning puncture casing pipe that matches with the said puncture needle;
(4) Mount the camera shooting module at the head end of the puncture needle. The head end of the said puncture needle is sheathed with a transparent cover that can cover camera shooting module;
(5) Insert the puncture needle in the positioning puncture casing pipe, and make a transparent cover at the head end of the said puncture needle slightly extend out of the said positioning puncture casing pipe to manufacture a disposable endoscopic puncture outfit for laparoscopy operations.

The said step (2) further comprises the following steps:
(2.1) Prepare a needle guard;
(2.2) Prepare a handle;
(2.3) Prepare a protective rod;
(2.4) Prepare a reset spring;
(2.5) A sleeve joint part that matches with the needle guard is set on the front side wall of the handle. The tail end of the needle guard is sheathed on the sleeve joint part of the handle to make the head end of the said needle guard form a single bevel blade. The tilting angle of the bevel of the said blade is between 20~70 degrees.
(2.6) A mounting rack that matches with the camera shooting module is mounted at the head end of the protective rod. Mounting positions that match with the transparent cover are reserved at the head end of the said mounting rack.
(2.7) A boss is set in the middle of the protective rod. The reset spring is sheathed at the tail end of the protective rod, the tail end of the said protective rod is inserted in the needle guard to pass through the sleeve joint part and stretch into the handle. One end of reset spring on the said protective rod presses against the sleeve joint part while the other end presses against the boss. Moreover, a clamping cap is set at the tail end of the protective rod to prevent it from moving out of the handle. A puncture needle is thus manufactured.

The said step (2) further comprises the following steps:
(2.8) Prepare a protection mechanism;
(2.9) The said protection mechanism is set in the handle of the puncture needle and can prevent the transparent cover from withdrawing back into the needle guard when the puncture needle is not used. If the puncture needle is used with the positioning puncture casing pipe, a protection function will be automatically started to prevent the needle guard that stretches into the abdominal cavity from accidentally injuring the visceral organs.

The said step (3) further comprises the following steps:
(3.1) Prepare a sealing gasket: a buckle is set on the outer edge of the said sealing gasket. The middle part of the sealing gasket has a conical bulge in a side. A through-hole that matches with the said needle guard is set at the central position of the said bulge. The said through-hole has an interference fit with the said needle guard.
(3.2) Prepare a check valve made with flexible material. A hook is set on the outer edge of the said check valve. Two anti-pressing plates are set in the middle part of the check valve. The two anti-pressing plates are set oppositely in a closing shape to form an elongated gap that matches with the said needle guard between their two adjacent end faces. A convex rib is set respectively on the inner sides of the two anti-pressing plates to strength their structural strength. When the said needle guard is moved out of the elongated gap, the said convex rib can have the two adjacent end faces of the two anti-pressing plates closely pressed against each other to prevent the high-pressure gas in the abdominal cavity from leaking.
(3.3) Prepare a casing pipe sheath made with high polymer material. A cavity that matches with the contour of the said check valve is formed at the tail end of the said casing pipe sheath. The head end of the said casing pipe sheath extends at its axial direction, and its outer side is set with a nodular and conical bulge. The head end of the said casing pipe sheath is in a conical shape.
(3.4) Place the said check valve in the cavity of the said casing pipe sheath, and have the hook of the said check valve buckled on the opening of the said cavity.
(3.5) Have the sealing gasket set on the opening of the cavity, and have the buckle of the said sealing gasket buckled on the hook of the check valve.

(3.6) Prepare an upper cover, have the said upper cover fastened on the opening of the said cavity, and have the said sealing gasket and the check valve positioned in the cavity of the casing pipe sheath.

(3.7) Prepare a two-way valve, have the said two-way valve fixed on the said casing pipe sheath, and have the said two-way valve and the cavity of the said casing pipe sheath connected to manufacture a positioning puncture casing pipe.

The said transparent cover is a round pipe body whose one end is closed. The closing part of the said round pipe body is in a beveled, spherical, conical or polygonal pyramid shape. When the closing part of the said round pipe body is in a beveled shape, the tilting angle of its bevel is 20~70 degrees.

A puncture outfit made with a method for manufacturing a disposable endoscopic puncture outfit for laparoscopy operations comprises a camera shooting module with light source, a puncture needle and a positioning puncture casing pipe that matches with the said puncture needle. The said camera shooting module is set at the head end of the puncture needle. The head end of the said puncture needle is sheathed with a transparent cover that can cover camera shooting module. The said puncture needle is inserted in the positioning puncture casing pipe to make the transparent cover at the head end of the said puncture needle slightly extend out of the said positioning puncture casing pipe.

The said puncture needle comprises a needle guard, a handle, a protective rod and a reset spring. A sleeve joint part that matches with the needle guard is set on the front side wall of the handle. The tail end of the needle guard is sheathed on the sleeve joint part of the handle to make the head end of the said needle guard form a single bevel blade. The tilting angle of the bevel of the said blade is between 20~70 degrees. A mounting rack that matches with the camera shooting module is mounted at the head end of the protective rod. Mounting positions that match with the transparent cover are reserved at the head end of the said mounting rack. A boss is set in the middle of the protective rod. The tail end of the said protective rod is inserted in the needle guard to pass through the sleeve joint part and stretch into the handle. Moreover, a clamping cap is set at the tail end of the protective rod to prevent it from moving out of the handle. The reset spring is sheathed at the tail end of the protective rod, and one end of the said reset spring presses against the sleeve joint part while the other end presses against the boss.

The said puncture needle further comprises a protection mechanism. The said protection mechanism comprises an elastic arm whose head end is fixed in the handle. The middle part of the elastic arm is set with a clamping position that can block the clamping cap to prevent the transparent cover from withdrawing back into the needle guard when the puncture needle is not used. The tail end of the elastic arm extends out from the front side wall of the handle to form a dial piece that presses against the said positioning puncture casing pipe to make the clamping position move out of from the clamping cap when the puncture needle is matched with the positioning puncture casing pipe.

The said positioning puncture casing pipe comprises a casing pipe sheath, an upper cover, a sealing gasket, a check valve and a two-way valve. A buckle is set on the outer edge of the said sealing gasket. The middle part of the sealing gasket has a conical bulge in a side. A through-hole that matches with the said needle guard is set at the central position of the said bulge. The said through-hole has an interference fit with the said needle guard. A hook is set on the outer edge of the said check valve. Two anti-pressing plates are set in the middle part of the check valve. The two anti-pressing plates are set oppositely in a closing shape to form an elongated gap that matches with the said needle guard between their two adjacent end faces. A convex rib is set respectively on the inner sides of the two anti-pressing plates to strength their structural strength. A cavity that matches with the contour of the said check valve is formed at the tail end of the said casing pipe sheath. The head end of the said casing pipe sheath extends at its axial direction, and its outer side is set with a nodular and conical bulge. The head end of the said casing pipe sheath is in a conical shape. The said check valve is set in the cavity of the casing pipe sheath, and the hook of the said check valve is buckled on the opening of the said cavity. The said sealing gasket is set on the opening of the cavity, and the buckle of the said sealing gasket is buckled on the hook of the check valve. The said upper cover is fastened on the opening of the said cavity, and the said sealing gasket and the check valve are positioned in the cavity of the casing pipe sheath. The said two-way valve is fixed on the said casing pipe sheath, and the said two-way valve and the cavity of the said casing pipe sheath are connected each other.

The said transparent cover is a round pipe body whose one end is closed. The closing part of the said round pipe body is in a beveled, spherical, conical or polygonal pyramid shape. When the closing part of the said round pipe body is in a beveled shape, the tilting angle of its bevel is 20~70 degrees.

Beneficial effects of this invention: The manufacturing method provided by this invention has a simple process, is easy to implement, and has high production efficiency. The puncture outfit provided by this invention is designed smartly, has a reasonable structure and can be used for visible surgical procedures through the camera shooting module, and can prevent the normal tissues or viscera from being accidentally injured in blind sight, effectively improve the safety of the puncture surgery and reduce the medical negligence. Moreover, the operation can be carried out in a visible state, which can greatly shorten the duration of surgery and reduce the pain of patients. It features simple operation and low cost, and lies less on the skill of a surgeon, and the accuracy and success rate of the surgery can be increased.

A nodular and conical bulge is set on the casing pipe sheath. It has good fixity and does not slip, which can avoid the common safety incident due to easy slipping. Moreover, the head end of the casing pipe sheath is in a conical shape, which can reduce the resistance during puncturing and further relieve the incision injury. It is operated conveniently and can realize the minimally invasive effect. Moreover, it features simple entire structure, easy implementation, low cost and disposable use. It can avoid cross infection and ensure the safe use.

The head end of the said needle guard forms a single bevel blade. The tilting angle of the bevel of the said blade is between 20~70 degrees. Its blade can be effectively used to incise the tissues. Hole is expanded along the titling angle. It brings minor injury and effectively improves the safety and effectiveness of the puncture surgery.

Further explanation for this invention is given through the following figures and embodiments.

DETAILED DESCRIPTION OF THE INVENTION

Figure 1:
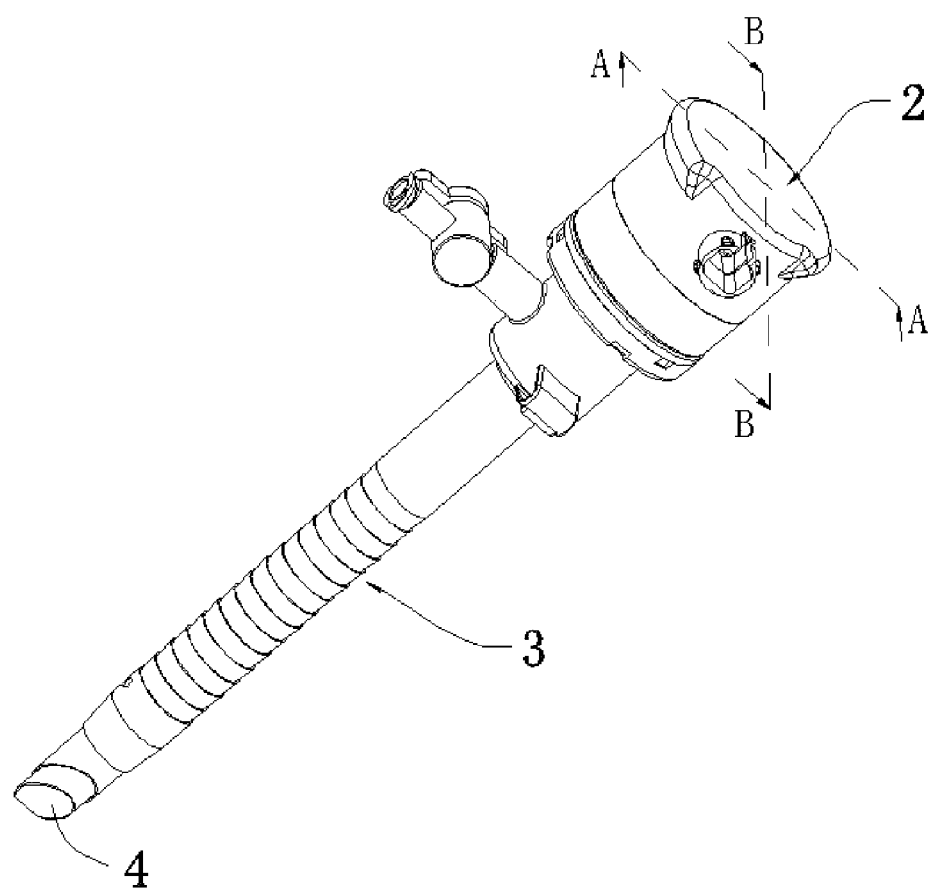
FIG. 1 is a solid structure diagram of this invention.
Figure 2:
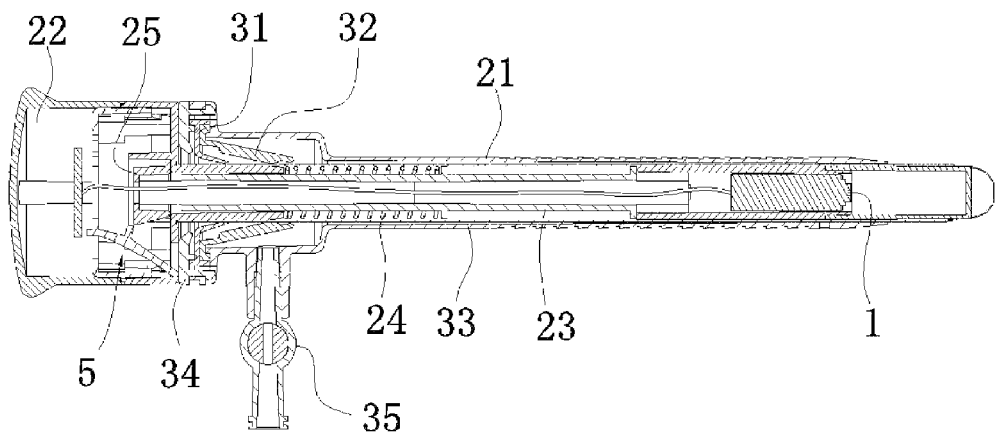
FIG. 2 is an A-A section structure diagram in FIG. 1.
Figure 3:
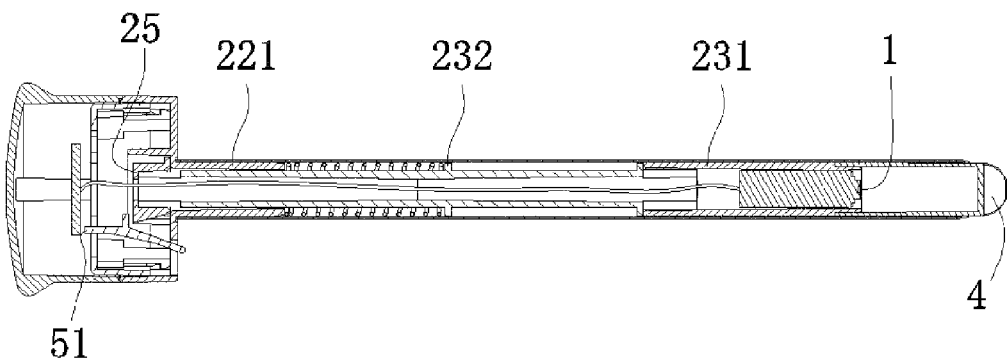
FIG. 3 is an A-A section structure diagram of puncture needle in FIG. 1.
Figure 4:
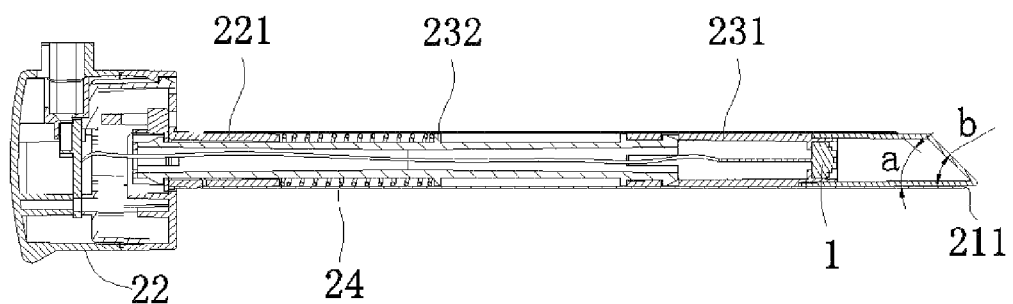
FIG. 4 is a B-B section structure diagram of puncture needle in FIG. 1.
Figure 5:
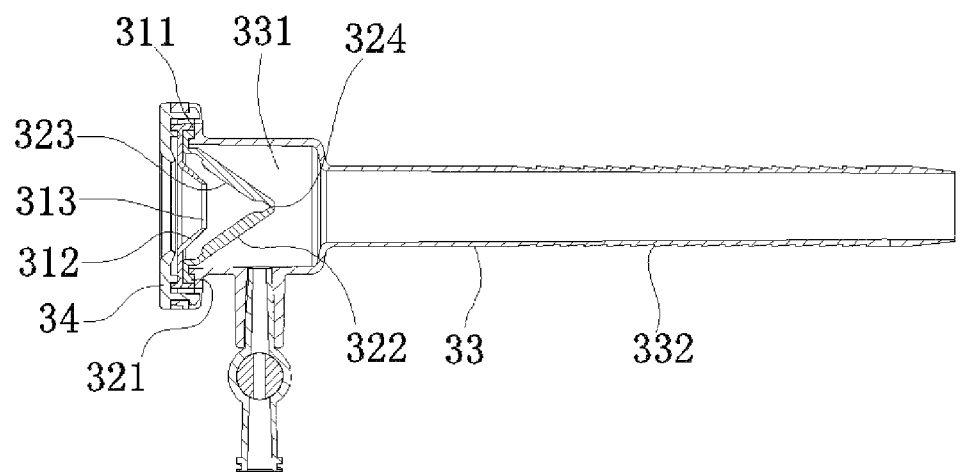
FIG. 5 is an A-A section structure diagram of positioning puncture casing pipe in FIG. 1.
Figure 6:
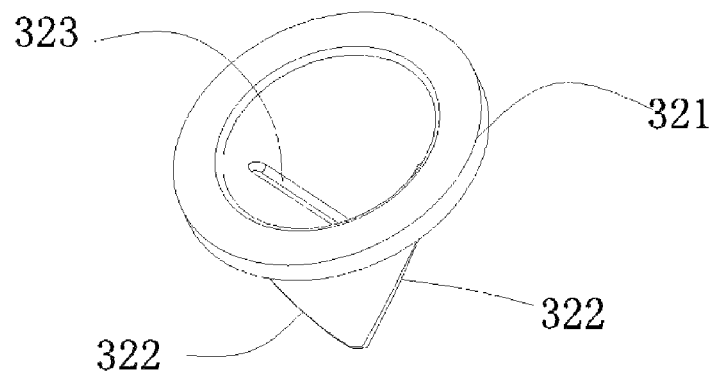
FIG. 6 is a structure diagram of check valve in FIG. 1.

Embodiment: Refer to FIG. 1-6. This invention embodiment provides a method for manufacturing a disposable endoscopic puncture outfit for laparoscopy operations, characterized in that it comprises the following steps:

(1) Prepare a camera shooting module with light source 1;

(2) Prepare a puncture needle 2;

(3) Prepare a positioning puncture casing pipe 3 that matches with the said puncture needle 2;

(4) Mount the camera shooting module 1 at the head end of the puncture needle 2. The head end of the said puncture needle 2 is sheathed with a transparent cover 4 that can cover camera shooting module 1;

(5) Insert the puncture needle 2 in the positioning puncture casing pipe 3, and make a transparent cover 4 at the head end of the said puncture needle 2 slightly extend out of the said positioning puncture casing pipe 3 to manufacture a disposable endoscopic puncture outfit for laparoscopy operations.

The said step (2) further comprises the following steps:

(2.1) Prepare a needle guard 21;

(2.2) Prepare a handle 22;

(2.3) Prepare a protective rod 23;

(2.4) Prepare a reset spring 24;

(2.5) A sleeve joint part 221 that matches with the needle guard 21 is set on the front side wall of the handle 22. The tail end of the needle guard 21 is sheathed on the sleeve joint part 221 of the handle to make the head end of the said needle guard 21 form a single bevel blade 211. The tilting angle a of the bevel of the said blade 211 is between 20~70 degrees.

(2.6) A mounting rack 231 that matches with the camera shooting module 1 is mounted at the head end of the protective rod 23. Mounting positions that match with the transparent cover 4 are reserved at the head end of the said mounting rack 231.

(2.7) A boss 232 is set in the middle of the protective rod 23. The reset spring 24 is sheathed at the tail end of the protective rod 23, the tail end of the said protective rod 23 is inserted in the needle guard 21 to pass through the sleeve joint part 221 and stretch into the handle 22. One end of reset spring 24 on the said protective rod 23 presses against the sleeve joint part 221 while the other end presses against the boss 232. Moreover, a clamping cap 25 is set at the tail end of the protective rod 23 to prevent it from moving out of the handle 22. A puncture needle 2 is thus manufactured.

(2.8) Prepare a protection mechanism 5;

(2.9) The said protection mechanism 5 is set in the handle 22 of the puncture needle 2 and can prevent the transparent cover 4 from withdrawing back into the needle guard 21 when the puncture needle 2 is not used. If the puncture needle 2 is used with the positioning puncture casing pipe 3, a protection function will be automatically started to prevent the needle guard 21 that stretches into the abdominal cavity from accidentally injuring the visceral organs.

The said step (3) further comprises the following steps:

(3.1) Prepare a sealing gasket 31: a buckle 311 is set on the outer edge of the said sealing gasket 31. The middle part of the sealing gasket has a conical bulge 312 in a side. A through-hole 313 that matches with the said needle guard 21 is set at the central position of the said bulge 312. The said through-hole 313 has an interference fit with the said needle guard 21.

(3.2) Prepare a check valve 32 made with flexible material. A hook 321 is set on the outer edge of the said check valve 32. Two anti-pressing plates 322 are set in the middle part of the check valve. The two anti-pressing plates 322 are set oppositely in a closing shape to form an elongated gap 324 that matches with the said needle guard 21 between their two adjacent end faces. A convex rib 323 is set respectively on the inner sides of the two anti-pressing plates 322 to strength their structural strength. When the said needle guard 21 is moved out of the elongated gap 324, the said convex rib 323 can have the two adjacent end faces of the two anti-pressing plates 322 closely pressed against each other to prevent the high-pressure gas in the abdominal cavity from leaking.

(3.3) Prepare a casing pipe sheath 33 made with high polymer material. A cavity 331 that matches with the contour of the said check valve 32 is formed at the tail end of the said casing pipe sheath 33. The head end of the said casing pipe sheath 33 extends at its axial direction, and its outer side is set with a nodular and conical bulge 332. The head end of the said casing pipe sheath 33 is in a conical shape.

(3.4) Place the said check valve 32 in the cavity 331 of the said casing pipe sheath 33, and have the hook 321 of the said check valve 32 buckled on the opening of the said cavity 331.

(3.5) Have the sealing gasket 31 set on the opening of the cavity 331, and have the buckle 311 of the said sealing gasket 31 buckled on the hook 321 of the check valve 32.

(3.6) Prepare an upper cover 34, have the said upper cover 34 fastened on the opening of the said cavity 331, and have the said sealing gasket 31 and the check valve 32 positioned in the cavity 331 of the casing pipe sheath 33.

(3.7) Prepare a two-way valve 35, have the said two-way valve 35 fixed on the said casing pipe sheath 33, and have the said two-way valve 35 and the cavity 331 of the said casing pipe sheath 31 connected to manufacture a positioning puncture casing pipe 3.

The said transparent cover 4 is a round pipe body 41 whose one end is closed. The closing part 42 of the said round pipe body 41 is in a beveled, spherical, conical or polygonal pyramid shape. When the closing part 42 of the said round pipe body 41 is in a beveled shape, the tilting angle b of its bevel is 20~70 degrees.

A puncture outfit made with a method for manufacturing a disposable endoscopic puncture outfit for laparoscopy operations comprises a camera shooting module with light source 1, a puncture needle 2 and a positioning puncture casing pipe 3 that matches with the said puncture needle 2. The said camera shooting module 1 is set at the head end of the puncture needle 2. The head end of the said puncture needle 2 is sheathed with a transparent cover 4 that can cover camera shooting module 1. The said puncture needle 2 is inserted in the positioning puncture casing pipe 3 to make the transparent cover 4 at the head end of the said puncture needle 2 slightly extend out of the said positioning puncture casing pipe 3. The said transparent cover 4 is a round pipe body 41 whose one end is closed. The closing part 42 of the said round pipe body 41 is in a beveled, spherical, conical or polygonal pyramid shape. When the closing part 42 of the said round pipe body 41 is in a beveled shape, the tilting angle b of its bevel is 20~70 degrees.

The said puncture needle 2 comprises a needle guard 21, a handle 22, a protective rod 23 and a reset spring 24. A sleeve joint part 221 that matches with the needle guard 21 is set on the front side wall of the handle 22. The tail end of the needle guard 21 is sheathed on the sleeve joint part 221 of the handle 22 to make the head end of the said needle guard 21 form a single bevel blade 211\hat matches with the camera shooting module 1 is mounted at the head end of the protective rod 23. Mounting positions that match with the transparent cover 4 are reserved at the head end of the said mounting rack 231. A boss 232 is set in the middle of the protective rod 23. The tail end of the said protective rod 23 is inserted in the needle guard 21 to pass through the sleeve joint part 221 and stretch into the handle 22. Moreover, a clamping cap 25 is set at the tail end of the protective rod 23 to prevent it from moving out of the handle 22. The reset spring 24 is sheathed at the tail end of the protective rod 23, and one end of the said reset spring 24 presses against the sleeve joint part 221 while the other end presses against the boss 232. The head end of the said needle guard 21 forms a single bevel blade 211. The tilting angle of the bevel of the said blade 211 is between 20~70 degrees. Its blade 211 can be effectively used to incise the tissues. Hole is expanded along the titling angle. It brings minor injury and effectively improves the safety and effectiveness of the puncture surgery.

The said puncture needle 2 further comprises a protection mechanism 5. The said protection mechanism 5 comprises an elastic arm 51 whose head end is fixed in the handle 22. The middle part of the elastic arm is set with a clamping position that can block the clamping cap 25 to prevent the transparent cover 4 from withdrawing back into the needle guard 21 when the puncture needle 2 is not used. The tail end of the elastic arm extends out from the front side wall of the handle 22 to form a dial piece that presses against the said positioning puncture casing pipe 3 to make the clamping position move out of from the clamping cap 25 when the puncture needle 2 is matched with the positioning puncture casing pipe 3.

The said positioning puncture casing pipe 3 comprises a casing pipe sheath 33, an upper cover 34, a sealing gasket 31, a check valve 32 and a two-way valve 35. A buckle 311 is set on the outer edge of the said sealing gasket 31. The middle part of the sealing gasket has a conical bulge 312 in a side. A through-hole 313 that matches with the said needle guard 21 is set at the central position of the said bulge 312. The said through-hole 313 has an interference fit with the said needle guard 21. A hook 321 is set on the outer edge of the said check valve 32. Two anti-pressing plates 322 are set in the middle part of the check valve. The two anti-pressing plates 322 are set oppositely in a closing shape to form an elongated gap 324 that matches with the said needle guard 21 between their two adjacent end faces. A convex rib 323 is set respectively on the inner sides of the two anti-pressing plates 322 to strength their structural strength. A cavity 331 that matches with the contour of the said check valve 32 is formed at the tail end of the said casing pipe sheath 33. The head end of the said casing pipe sheath 33 extends at its axial direction, and its outer side is set with a nodular and conical bulge 332. The head end of the said casing pipe sheath 33 is in a conical shape. The said check valve 32 is set in the cavity 331 of the casing pipe sheath 33, and the hook 321 of the said check valve 32 is buckled on the opening of the said cavity 331. The said sealing gasket 31 is set on the opening of the cavity 331, and the buckle 311 of the said sealing gasket 31 is buckled on the hook 321 of the check valve 32. The said upper cover 4 is fastened on the opening of the said cavity 331, and the said sealing gasket 31 and the check valve 32 are positioned in the cavity 331 of the casing pipe sheath 33. The said two-way valve 35 is fixed on the said casing pipe sheath 33, and the said two-way valve 35 and the cavity 331 of the said casing pipe sheath 33 are connected each other.

Figure 7:
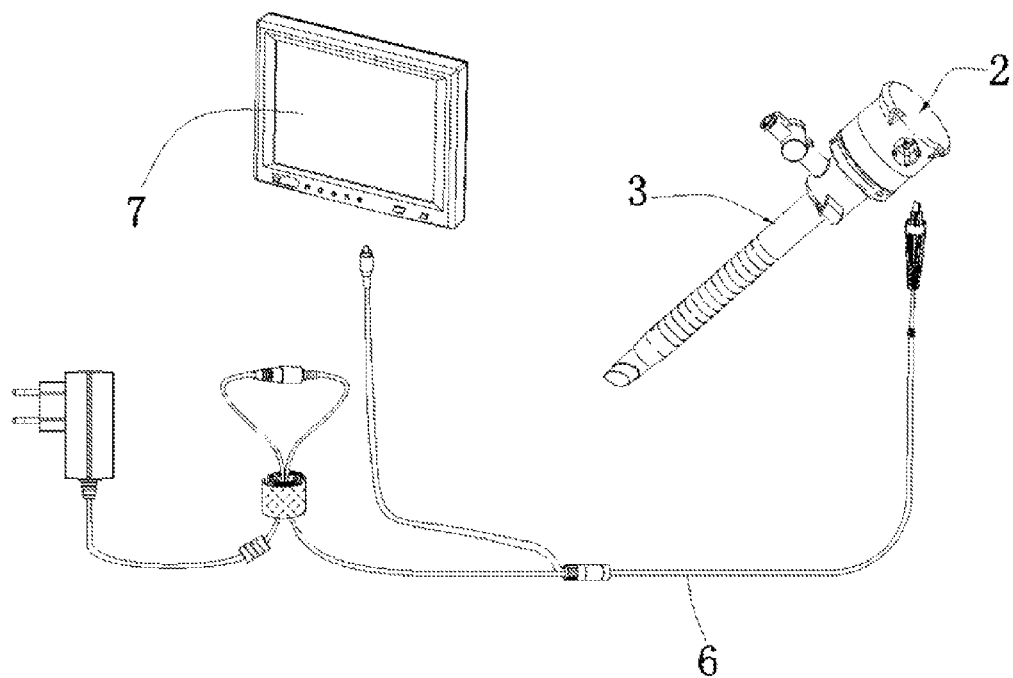
FIG. 7 is a state structure diagram during the use of this invention.

Refer to FIG. 7: Before puncturing, the power socket of video connecting cable 6 is plugged into power socket of power supply system. One end of the video connecting cable 6 is connected with the camera shooting module 1 on the puncture needle 2 while the other end of the video connecting cable is connected to the input port of display unit 7. The puncture needle 2 is inserted in the said positioning puncture casing pipe 3 to make the puncture needle 2 match with the positioning puncture casing pipe 3. At this moment, the dial piece on the elastic arm 51 rotates at a certain angle with axis of the joint between the elastic arm 51 and the handle 22 under the pressure of the upper cover 34 of the positioning puncture casing pipe 3. The clamping position of elastic arm 51 moves out of the movement direction of the protective rod 23 from the clamping cap 25, and then the clamping cap 25 of the protective rod 23 can move towards one side of the handle 22.

During puncturing, the transparent cover 4 of the puncture needle 2 overcomes the elastic force of the reset spring 24 and retracts in the needle guard 21 under the resistance from the skin, then the blade 211 of the needle guard 21 exposes. At this moment, the said blade 211 is used to incise the skin tissues to make the puncture needle 2 enter the tissues slowly. Under the lighting of light source, the camera shooting module 1 can deliver the images for the real-time process of puncturing the tissues and entering the abdominal cavity to the display unit 7 through the video connecting cable. The artery blood vessels such as retroperitoneal aorta and artery blood vessels of abdominal wall cannot be seen effectively. It is operated conveniently and avoids the surgery incidents, which effectively improves the safety and effectiveness of the puncture surgery.

During puncturing, the transparent cover 4 will reset itself under the spring force of the reset spring 24 as the resistance of the transparent cover 4 disappears. The state that the transparent cover 4 slightly extends out of the positioning puncture casing pipe is recovered to act as a protection function. At this moment, even though the puncturing of abdominal cavity is continued due to misoperation, it can prevent the blade 211 of the needle guard 21 from injuring the visceral organs under the function of the transparent cover 4. This has greatly improves the safety and effectiveness of the puncture surgery. Meanwhile, the nodular and conical bulge 332 of the casing pipe sheath 33 enters the abdominal cavity to have the casing pipe sheath 33 firmly fixed on the abdominal wall under the combined function of contractility formed between the nodular and conical bulge 332 and the incision expansion. The gas can be delivered into the abdominal cavity by connecting the two-way valve 35 and the pneumoperitoneum apparatus so as to maintain the air pressure of abdomen during surgery. Moreover, the principal part of puncture outfit is made with high polymer material. Its disposable use can avoid cross infection and ensure the safe use.

Figure 8:
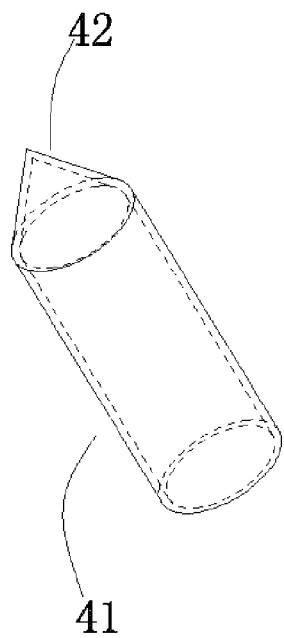
FIG. 8 is a structure diagram 1 of transparent cover in FIG. 1.
Figure 9:
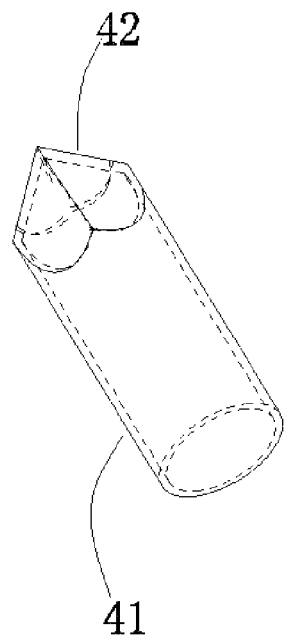
FIG. 9 is a structure diagram 2 of transparent cover in FIG. 1.
Figure 10:
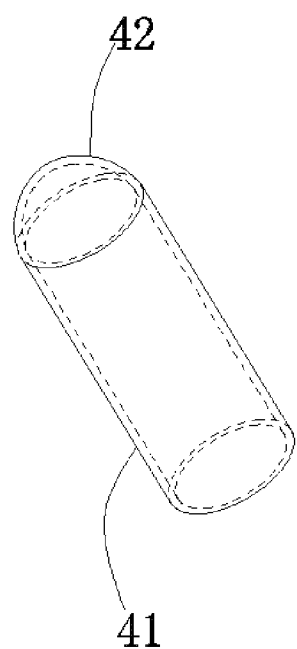
FIG. 10 is a structure diagram 3 of transparent cover in FIG. 1.

In this embodiment, the said transparent cover 4 is a round pipe body 41 whose one end is closed. When the closing part 42 of the said round pipe body 41 is in a beveled shape, the tilting angle of its bevel is 20~70 degrees. It has the functions of puncturing and protection. In other embodiments, referring to FIG. 8-9, the closing part 42 of the said round pipe body 41 is in a conical or polygonal pyramid shape and can replace the blade 211 of the needle guard 21 and be directly used for puncturing. Referring to FIG. 10, the closing part 42 of the said round pipe body 41 can be set as a spherical shape. This can effectively prevent extremely easy injuries against the normal tissues of visceral organs when the puncture outfit is inserted in the abdominal cavity, avoid laparoscopic surgery complications such as vascular, intestine and bladder injuries and guarantee the surgery safety and effectiveness.

As described in the above embodiments for this invention, other puncture outfits and their manufacturing methods by the adoption of the same or similar structures are within the protective scope of this invention.

What is claimed is:

1. A method for manufacturing a disposable endoscopic puncture outfit for laparoscopy operations comprising the following steps:
   mounting a camera shooting module with a light source at a head end of a puncture needle;
   sheathing a transparent cover that covers the camera shooting module at the head end of the puncture needle;
   inserting the puncture needle in a positioning puncture casing pipe that matches with the puncture needle, and extending the transparent cover at the head end of the puncture needle slightly out of the positioning puncture casing pipe;
   wherein the puncture needle which comprises a needle guard, a handle, a protective rod and a reset spring is manufactured according to the following steps:
   forming a head end of the needle guard as a single bevel blade having a bevel with a tilted angle of 20-70 degrees;
   mounting a mounting rack that matches with the camera shooting module at a head end of the protective rod; whereas mounting positions that match with the transparent cover are reserved at the head end of the mounting rack;
   fixing one side of a sleeve joint part that matches with the needle guard on a front side wall of the handle; sheathing a tail end of the needle guard on another end of the sleeve joint part; pressing one end of the reset spring against said another end of the sleeve joint part;
   fixing a boss in the middle of the protective rod; sheathing the reset spring at a tail end of the protective rod; inserting the tail end of the protective rod in the needle guard so that the protective rod passes through the sleeve joint part and extends into the handle; pressing another end of the reset spring against the boss; and providing a clamping cap at the tail end of the protective rod to prevent the protective rod from moving out of the handle.

2. The method for manufacturing a disposable endoscopic puncture outfit for laparoscopy operations as set forth in claim 1, wherein the method also comprises the following steps:
   providing a protection mechanism at the handle of the puncture needle to prevent the transparent cover from withdrawing back into the needle guard when the puncture needle is not used.

3. The method for manufacturing a disposable endoscopic puncture outfit for laparoscopy operation as set forth in claim 2, wherein the positioning puncture casing pipe comprising a casing pipe sheath made of high polymer material, an upper cover, a sealing gasket, a check valve made with flexible material and a two-way valve is manufactured according to the following steps: providing a buckle on an outer edge of the sealing gasket which has a conical bulge at one side of a middle part thereof; whereas a central position of the conical bulge has a through-hole that matches with the needle guard and the through-hole has an interference fit with the needle guard; providing a hook on an outer edge of the check valve and providing two anti-pressing plates in a middle part of the check valve; whereas the two anti-pressing plates are positioned oppositely in a closing shape to form an elongated gap that matches with the needle guard between their two adjacent end faces; providing a convex rib respectively on inner sides of the two anti-pressing plates to strengthen their structural; forming a cavity that matches with a contour of the check valve at a tail end of the casing pipe sheath; extending a head end of the casing pipe sheath along an axial direction thereof and providing a nodular and conical bulge at an outer side thereof whereas the head end of the casing pipe sheath is formed in a conical shape; placing the check valve in the cavity of the casing pipe sheath and buckling the hook of the check valve on an opening of the cavity; positioning the sealing gasket on the opening of the cavity, and buckling the buckle of the sealing gasket on the hook of the check valve; fastening the upper cover on the opening of the cavity, and positioning the sealing gasket and the check valve in the cavity of the casing pipe sheath; and fixing the two-way valve on the casing pipe sheath, and connecting the two-way valve to the cavity of the casing pipe sheath.

* * * * *